United States Patent [19]

Chou

[11] 4,165,316

[45] Aug. 21, 1979

[54] PROCESS FOR PREPARING SULFINYL CHLORIDES FROM PENICILLIN SULFOXIDES

[75] Inventor: Ta-Sen Chou, Indianapolis, Ind.

[73] Assignee: Eli Lilly and Company, Indianapolis, Ind.

[21] Appl. No.: 858,506

[22] Filed: Dec. 8, 1977

Related U.S. Application Data

[62] Division of Ser. No. 696,674, Jun. 16, 1976, Pat. No. 4,075,203.

[51] Int. Cl.$^2$ .................. C07D 205/08; C07D 501/10
[52] U.S. Cl. .......................... 260/239 A; 260/307 H; 260/326 S; 260/326.37; 260/330.3; 544/18
[58] Field of Search ..... 260/239 AL, 307 H, 332.2 H

[56] References Cited

U.S. PATENT DOCUMENTS 4,071,513  1/1978  Kim .................. 260/239 AL

OTHER PUBLICATIONS

Ishimara et al., Bull. Chem. Soc., Japan 48, 2989–2990 (1975).

Primary Examiner—Mark L. Berch
Attorney, Agent, or Firm—William C. Martens, Jr.; Everet F. Smith

[57] ABSTRACT

A penicillin sulfoxide ester is reacted with an N-chloro halogenating agent at a temperature of from about 75° C. to about 135° C. and in the presence of an alkylene oxide and calcium oxide to produce a 2-chlorosulfinylazetidin-4-one intermediate. The intermediate, upon separation from the alkylene oxide, calcium oxide, and any conversion products of both the alkylene oxide and calcium oxide, can be treated with stannic chloride to produce a 3-exomethylenecepham sulfoxide.

18 Claims, No Drawings

PROCESS FOR PREPARING SULFINYL CHLORIDES FROM PENICILLIN SULFOXIDES

This is a division of application Ser. No. 696,674, filed June 12, 1976, now U.S. Pat. No. 4,075,203.

BACKGROND OF THE INVENTION

In the recently issued U.S. Pat. No. 3,843,682 there is disclosed a process for preparing 3-methyl-2-(2-chlorosulfinyl-4-oxo-3-imido-1-azetidinyl)-3-butenoate esters, variously termed "2-chlorosulfinyl-3-imido-azetidin-4-ones". These compounds are prepared from the corresponding penicillin sulfoxide esters by reaction of the latter with sulfuryl chloride at a temperature of from about 75° C. to about 120° C. The compounds which are prepared by this known process are exclusively the 3-imido substituted 2-chlorosulfinylazetidin-4-ones since the process is limited to the use of the 6-imido penicillin sulfoxide esters as starting material. There is no disclosure of the use of or the possibility to use the 6-amido penicillin sulfoxide esters, including the conveniently obtainable penicillin sulfoxide derivatives of the naturally occurring Penicillin G and/or Penicillin V. When one attempts to carry out the reaction disclosed in U.S. Pat. No. 3,843,682 using a 6-amido penicillin sulfoxide ester as starting material, the product which is obtained is a complex mixture containing no 2-chlorosulfinylazetidin-4-one product, or, at most, the latter in a quantity so minute as to be undetectable by ordinary analytical techniques. Therefore, this previously disclosed method has significant deficiencies since it requires the absence of an amide hydrogen in the 6-position of the penicillin sulfoxide starting material.

In co-pending Application Ser. No. 673,017 filed Apr. 2, 1976, now U.S. Pat. No. 4,081,440 a method for preparing sulfinyl chloride intermediates from 6-amido penicillin sulfoxide esters is provided. This method involves treating the penicillin sulfoxide with an N-chloro halogenating agent at a temperature of about 75° C. to about 135° C.

It now has become apparent that the degree of conversion of the 6-amido penicillin sulfoxide to the sulfinyl chloride in accordance with the reaction described in Application Ser. No. 673,017 diminishes considerably when the reaction scale is increased beyond typical research laboratory quantities, for example, in those instances in which 50 grams or more of the penicillin sulfoxide starting material are employed.

This invention is directed to the discovery that, in a large scale reaction (about 100 millimoles or more), the extent of conversion of a 6-amido penicillin sulfoxide to its corresponding sulfinyl chloride can be substantially increased by carrying out the reaction under specified conditions.

The 2-chlorosulfinylazetidin-4-ones produced by the process of this invention can be ring closed to produce a 3-exomethylenecepham sulfoxide ester. Cyclization of the 2-chlorosulfinylazetidin-4-ones to their corresponding 3-exomethylenecepham sulfoxides is accomplished by a Friedel-Crafts catalyst induced intramolecular reaction involving the sulfinyl chloride and the olefinic moieties of the azetidin-4-one starting material. This reaction generally is carried out using stannic chloride as Friedel-Crafts catalyst.

SUMMARY OF THE INVENTION

This invention is directed to an improved process for preparing sulfinyl chlorides. It is an object therefore of this invention to provide in a process for preparing a sulfinyl chloride of the formula

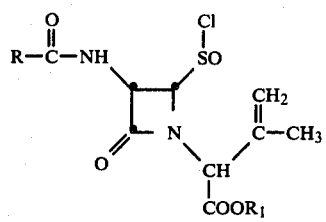

by reacting a penicillin sulfoxide of the formula

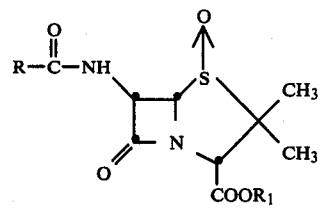

with an N-chloro halogenating agent at a temperature of from about 75° C. to about 135° C. in an inert solvent under anhydrous conditions and in the presence of an epoxide compound of the formula

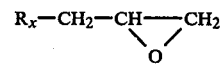

in which $R_x$ is hydrogen or methyl; and in which, in the above formulae, $R_1$ is a carboxylic acid protecting group; and R is (a) hydrogen, $C_1$-$C_3$ alkyl, halomethyl, cyanomethyl, benzyloxy, 4-nitrobenzyloxy, t-butyloxy, 2,2,2-trichloroethoxy, 4-methoxybenzyloxy, 3-(2-chlorophenyl)5-methylisoxazol-4-yl;

(b) the group R' in which R' is phenyl or phenyl substituted with 1 or 2 halogens, protected hydroxy, nitro, cyano, trifluoromethyl, $C_1$-$C_4$ alkyl, or $C_1$-$C_4$ alkoxy;

(c) a group of the formula R"—(Q)$_m$—CH$_2$— in which R" is R' as defined above, 1,4-cyclohexadienyl, 2-thienyl, or 3-thienyl; m is 0 or 1; and Q is O or S; subject to the limitation that when m is 1, R" is R'; or (d) a group of the formula

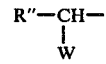

in which R" is as defined above, and W is protected hydroxy or protected amino; the improvement which comprises carrying out the reaction in the presence of calcium oxide.

This invention also is directed to a process for preparing 3-exomethylenecepham sulfoxides. It is a further object therefore of this invention to provide in a process for preparing a 3-exomethylenecepham sulfoxide of the formula

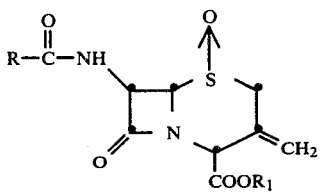

by (1) reacting a penicillin sulfoxide of the formula

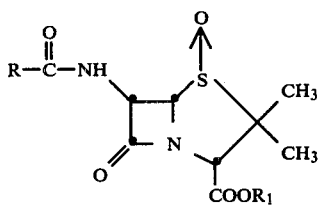

with an N-chloro halogenating agent at a temperature of from about 75° C. to about 135° C. in an inert solvent under anhydrous conditions and in the presence of an epoxide compound of the formula

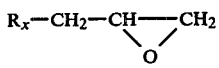

in which $R_x$ is hydrogen or methyl; and in which, in the above formulae, $R_1$ is a carboxylic acid protecting group; and R is (a) hydrogen, $C_1$-$C_3$ alkyl, halomethyl, cyanomethyl, benzyloxy, 4-nitrobenzyloxy, t-butyloxy, 2,2,2-trichloroethoxy, 4-methoxybenzyloxy, 3-(2-chlorophenyl)-5-methylisoxazol-4-yl;

(b) the group R' in which R' is phenyl or phenyl substituted with 1 or 2 halogens, protected hydroxy, nitro, cyano, trifluoromethyl, $C_1$-$C_4$ alkyl, or $C_1$-$C_4$ alkoxy;

(c) a group of the formula $R''$—$(Q)_m$—$CH_2$— in which R'' is R' as defined above, 1,4-cyclohexadienyl, 2-thienyl, or 3-thienyl; m is 0 or 1; and Q is O or S; subject to the limitation that when m is 1, R'' is R'; or (d) a group of the formula

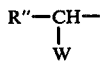

in which R'' is as defined above, and W is protected hydroxy or protected amino;

to produce a sulfinyl chloride of the formula

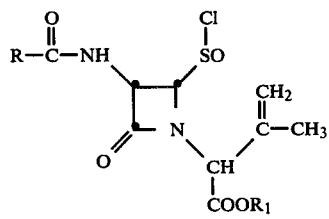

in which R and $R_1$ are as aforedefined;

(2) treating the resulting reaction mixture to remove said epoxide therefrom;

(3) filtering insolubles from the epoxide-free mixture; and (4) treating said epoxide-free mixture with a Friedel-Crafts catalyst at a temperature of from about −20° C. to about +100° C. to produce the aforementioned 3-exomethylenecepham sulfoxide; the improvement which comprises carrying out step (1) in the presence of calcium oxide.

DETAILED DESCRIPTION OF THE INVENTION

As delineated hereinabove, the process of this invention is directed to the preparation of sulfinyl chlorides of the formula

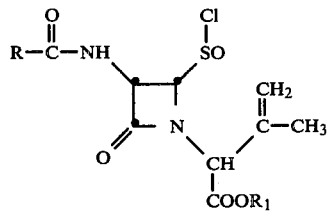

$R_1$ in the above formula denotes a carboxylic acid protecting group, and, preferably, one which is removable by acid treatment or by hydrogenation. Preferred carboxylic acid protecting groups include, for example, $C_4$-$C_6$ tert-alkyl, 2,2,2-trihaloethyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, dimethylallyl, phenacyl, or p-halophenacyl, in any of the above of which halo denotes chlorine, bromine or iodine.

Specific illustrations of the preferred carboxylic acid protecting groups of the sulfinyl chlorides produced by the process of this invention include, for example, t-butyl, t-amyl, t-hexyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like.

Preferred carboxylic acid protecting groups are t-butyl, benzyl, p-nitrobenzyl, p-methoxybenzyl, benzhydryl, and 2,2,2-trichloroethyl. Highly preferred groups are p-nitrobenzyl and 2,2,2-trichloroethyl, and, most preferably, p-nitrobenzyl.

The amide function of the sulfinyl chlorides prepared by the process of this invention has the formula

A preferred subclass of this amide function comprises those moieties in which R is (a) hydrogen, $C_1$-$C_3$ alkyl, halomethyl, cyanomethyl, benzyloxy, 4-nitrobenzyloxy, t-butyloxy, 2,2,2-trichloroethoxy, 4-methoxybenzyloxy, 3-(2-chlorophenyl)-5-methylisoxazol-4-yl;

(b) the group R' in which R' is phenyl or phenyl substituted with 1 or 2 halogens, protected hydroxy, nitro, cyano, trifluoromethyl, $C_1$-$C_4$ alkyl, or $C_1$-$C_4$ alkoxy; or (c) a group of the formula $R''$—$(Q)_m$—$CH_2$— in which R'' is R' as defined above, 1,4-cyclohexadienyl, 2-thienyl, or 3-thienyl; m is 0 or 1; and Q is O or S; subject to the limitation that when m is 1, R″ is R′.

Specific illustrations of the group R include, for example, hydrogen, methyl, ethyl, n-propyl, isopropyl, chloromethyl, bromomethyl, cyanomethyl, benzyloxy, 4-nitrobenzyloxy, t-butyloxy, 2,2,2-trichloroethoxy, 4-methoxybenzyloxy, phenyl, 2-chlorophenyl, 3,4-dichlorophenyl, 3-chloro-4-fluorophenyl, 3-formyloxyphenyl, 4-nitrophenyl, 2-cyanophenyl, 4-trifluoromethylphenyl, 3-methylphenyl, 2-ethylphenyl, 4-n-propylphenyl, 4-t-butylphenyl, 2-methoxyphenyl, 4-ethoxyphenyl, 3-isopropyloxyphenyl, 4-isobutyloxyphenyl, 1,4-cyclohexadienylmethyl, benzyl, 3-bromobenzyl, 2,5-dichlorobenzyl, 4-chloroacetoxybenzyl, 2-nitrobenzyl, 3-cyanobenzyl, 4-trifluoromethylbenzyl, 3-methylbenzyl, 4-n-butylbenzyl, 2-methoxybenzyl, 3-isopropoxybenzyl, phenoxymethyl, 3-iodophenoxymethyl, 4-fluorophenoxymethyl, 3-benzyloxyphenoxymethyl, 4-benzhydryloxyphenoxymethyl, 3-trityloxyphenoxymethyl, 4-nitrobenzyloxyphenoxymethyl, 4-trimethylsilyloxyphenoxymethyl, 3-nitrophenoxymethyl, 4-cyanophenoxymethyl, 2-trifluoromethylphenoxymethyl, 3-methylphenoxymethyl, 4-n-propylphenoxymethyl, 4-n-butylphenoxymethyl, 3-methoxyphenoxymethyl, 4-ethoxyphenoxymethyl, phenylthiomethyl, 3-iodophenylthiomethyl, 4-fluorophenylthiomethyl, 3-benzyloxyphenylthiomethyl, 4-benzhydryloxyphenylthiomethyl, 3-trityloxyphenylthiomethyl, 4-nitrobenzyloxyphenylthiomethyl, 4-trimethylsilyloxyphenylthiomethyl, 3-nitrophenylthiomethyl, 4-cyanophenylthiomethyl, 2-trifluoromethylphenylthiomethyl, 3-methylphenylthiomethyl, 4-n-propylphenylthiomethyl, 4-n-butylphenylthiomethyl, 3-methoxyphenylthiomethyl, 4-ethoxyphenylthiomethyl, α-(benzhydryloxy)-thien-2ylmethyl, α-(4-nitrobenzyloxy)-thien-2-ylmethyl, α-(t-butyloxycarbonylamino)-thien-2-ylmethyl, α-(formyloxy)-thien-3-ylmethyl, α-(benzyloxy)-thien-3-ylmethyl, α-(benzyloxycarbonylamino)-thien-3-ylmethyl, α-(chloroacetoxy)-thien-2-ylmethyl, α-(t-butyloxy)-thien-2-ylmethyl, α-(4-nitrobenzyloxycarbonylamino)-thien-2-ylmethyl, α-trityloxybenzyl, α-(4-methoxybenzyloxy)benzyl, α-(2,2,2-trichloroethoxycarbonylamino)benzyl, α-(trimethylsilyloxy)-4-bromobenzyl, α-(benzhydryloxycarbonylamino)-3-chlorobenzyl, α-(trimethylsilylamino)-4-fluorobenzyl, α,4-di(formyloxy)benzyl, α-(4-nitrobenzyloxycarbonylamino)-3-chloroacetoxybenzyl, α-(4-methoxybenzyloxycarbonylamino)-4-benzhydryloxybenzyl, α-benzyloxy-3-nitrobenzyl, α-(4-nitrobenzyloxy)-2-cyanobenzyl, α-(t-butoxycarbonylamino)-4-trifluoromethylbenzyl, α-formyloxy-4-methylbenzyl, α-benzyloxycarbonylamino-3-n-butylbenzyl, α-(benzyloxycarbonylamino)-4-methoxybenzyl, α-formyloxy-3-isopropoxybenzyl, thien-2-ylmethyl, thien-3-ylmethyl, 3-(2-chlorophenyl)-5-methylisoxazol-4-yl, and the like.

Of the groups defined by the term R, those which are especially preferred are those of the formula R″—(Q)$_m$—CH$_2$—. Of the latter class, highly preferred groups are those in which R″ is 2-thienyl or phenyl. When R″ is phenyl, it is more preferred that, when m is 1, Q is oxygen.

In portions of the definition provided herein for the group R, the terms "protected amino", "protected hydroxy", and "protected carboxy" are employed.

The term "protected amino", when employed herein, refers to an amino group substituted with one of the commonly employed amino blocking groups such as t-butyloxycarbonyl, benzyloxycarbonyl, 4-methoxybenzyloxycarbonyl, 4-nitrobenzyloxycarbonyl, 2,2,2-trichloroethoxycarbonyl, 1-carbomethoxy-2-propenyl formed with methyl acetoacetate, trimethylsilyl, and the like. Additional typical amino protecting groups are described by J. W. Barton in *Protective Groups in Organic Chemistry*, J. F. W. McOmie, Ed., Plenum Press, New York, N. Y., 1973, Chapter 2. Any of these are recognized as useful within the meaning of the term "protected amino" employed herein.

The term "protected hydroxy", when employed herein, refers to the readily cleavable groups formed with an hydroxyl group such as a formyloxy group, a chloroacetoxy group, a benzyloxy group, a benzhydryloxy group, a trityloxy group, a 4-nitrobenzyloxy group, a trimethylsilyloxy group, and the like. Other hydroxy protecting groups, including those described by C. B. Reese in *Protecting Groups in Organic Chemistry*, supra, Chapter 3, are considered to be within the term "protected hydroxy" as used herein.

The terms "protected carboxy" and "carboxylic acid protecting group", when employed herein, refer to a carboxy group which has been protected by one of the commonly used carboxylic acid protecting groups employed to block or protect the carboxylic acid functionality of a compound while a reaction or sequence of reactions involving other functional sites of the compound are carried out. Such protected carboxy groups are noted for their ease of cleavage to the corresponding carboxylic acid by hydrolytic or by hydrogenolytic methods. Examples of carboxylic acid protecting groups include t-butyl, benzyl, 4-methoxybenzyl, C$_2$-C$_6$ alkanoyloxymethyl, 2-iodoethyl, 4-nitrobenzyl, diphenylmethyl (benzhydryl), phenacyl, p-halophenacyl, dimethylallyl, 2,2,2-trichloroethyl, succinimidomethyl and like ester forming moieties. The nature of such ester forming groups is not critical so long as the ester formed therewith is stable under the reaction conditions of the process of this invention. Furthermore, other known carboxy protecting groups such as those described by E. Haslam in *Protective Groups in Organic Chemistry*, supra, Chapter 5, are considered to be within the term "protected carboxy" as used herein.

Preferred groups within the term "protected carboxy" are tert-butyl, p-methoxybenzyl, p-nitrobenzyl, benzhydryl, and 2,2,2-trichloroethyl.

In the foregoing definitions, hydroxy, amino, and carboxy protecting groups, of course, are not exhaustively described. The function of these groups is to protect reactive functional groups during preparation of a desired product. They then are removed without disruption of the remainder of the molecule. Many such protecting groups are well known in the art, and their use is equally applicable in the process of this invention.

As will be apparent to those of ordinary skill in the penicillin and cephalosporin arts, any of the penicillin sulfoxide starting materials used in the process of this invention are readily preparable from available penicillin sources such as naturally occurring Penicillin G and/or Penicillin V.

6-Aminopenicillanic acid (6-APA) can be prepared from either of the above naturally-occurring penicillins by cleavage of the 6-acyl function employing techniques well known in the art.

It is possible to prepare, by widely recognized techniques and from 6-APA, any of the starting materials of the process of this invention. For example, 6-APA can be converted to the desired ester of esterification of the 3-carboxyl function employing any of several typical esterification techniques.

Furthermore, the amino group of 6-APA can be acylated to produce any of the groups defined herein by the term

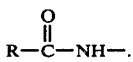

This is achieved by reacting 6-APA with an activated form of the acid of the intended acyl group. Such activated forms include the corresponding acid halides, anhydrides, or activated esters, such as the pentachlorophenyl ester.

Moreover, the penicillin can be oxidized to the sulfoxide under any of a wide variety of recognized conditions, including treatment of the penicillin with m-chloroperbenzoic acid or sodium periodate.

These conversions, cleavage to 6-APA, esterification, acylation, and oxidation, can be carried out in any sequence consistent with the intended structural modifications. In any event, all such conversions can be accomplished employing techniques, conditions, and reagents readily available to and well recognized by one of ordinary skill in the art.

Preferred penicillin sulfoxide esters for use in the process of this invention are those having the formula

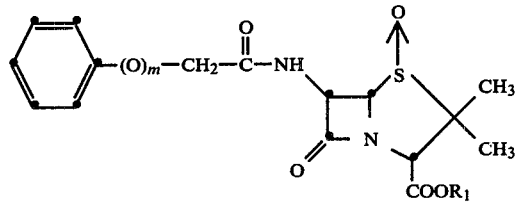

in which m is 0 or 1, and, preferably, is 1, and $R_1$ is a carboxylic acid protecting group, and, preferably, is p-nitrobenzyl.

Correspondingly, the preferred sulfinyl chlorides prepared from the above esters and by the process of this invention are those of the formula

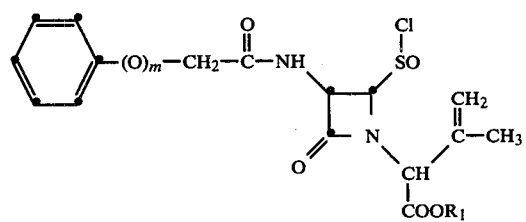

in which m is 0 or 1, and, preferably, is 1, and $R_1$ is a carboxylic acid protecting group, and, preferably, is p-nitrobenzyl.

Other preferred penicillin sulfoxide esters for use in the process of this invention are those of the formula

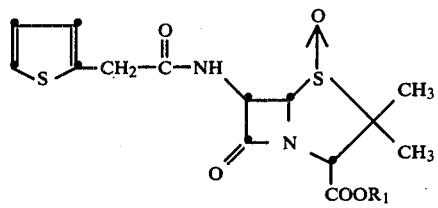

in which $R_1$ is a carboxylic acid protecting group, and, preferably, is p-nitrobenzyl.

Correspondingly, other preferred sulfinyl chlorides prepared from the above esters and by the process of this invention are those of the formula

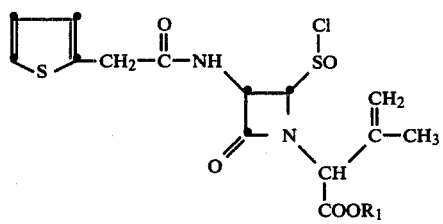

in which $R_1$ is a carboxylic acid protecting group, and, preferably, is p-nitrobenzyl.

The sulfinyl chlorides produced by the process of this invention result from the interaction of a penicillin sulfoxide ester with an N-chloro halogenating agent at an elevated temperature.

By the term "N-chloro halogenating agent" is meant a reagent having at least one chlorine bonded directly to a nitrogen atom with the remaining moiety or moieties of the structure of the reagent having electron-withdrawing strength sufficient to produce, as by-product from the sulfinyl chloride preparation, a nitrogen-containing compound which exhibits the following characteristics. The thus-produced nitrogen-containing compound, first, will be one which corresponds to the N-chloro halogenating agent but which has the chlorine atom replaced by a hydrogen atom. Secondly, the nitrogen-containing compound, due primarily to the properties of the electron-withdrawing moiety, will be inert to the sulfinyl chloride product.

The N-chloro halogenating agents which are employed in the process of this invention preferably are compounds of the formula

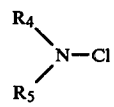

in which $R_4$ is hydrogen, chloro, $C_1$-$C_3$ alkyl, cyclohexyl, phenyl, or phenyl substituted with chloro, bromo, methyl, or nitro, and $R_5$ is $R_6$—X— in which $R_6$ is $C_1$-$C_3$ alkyl, cyclohexyl, phenyl, or phenyl substituted with chloro, bromo, methyl, or nitro, and X is

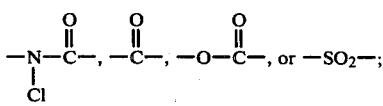

or R₄ and R₅ taken together with the nitrogen to which they are bonded define a heterocyclic structure of the formula

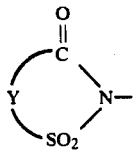

in which Y is o-phenylene or —(CH₂)ₙ— in which n is 2 or 3; or a structure of the formula

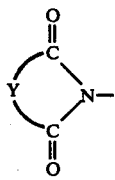

in which Y is as hereinbefore defined.

Several types of preferred N-chloro compounds which can be employed in producing the sulfinyl chlorides are described by the above definition. These N-chloro compounds include (a) ureas, (b) amides, (c) urethans, (d) sulfonamides, (e) sulfimides, and (f) imides.

The preferred N-chloro ureas which can be employed in this invention generally have the formula

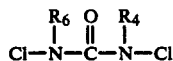

in which R₄ is hydrogen, chloro, C₁-C₃ alkyl, cyclohexyl, phenyl, or phenyl substituted with chloro, bromo, methyl, or nitro, and R₆ is C₁-C₃ alkyl, cyclohexyl, phenyl, or phenyl substituted with chloro, bromo, methyl, or nitro.

Illustrative of these ureas are

N,N′-dichloro-N-methylurea;
N,N′-dichloro-N-ethyl-N′-cyclohexylurea;
N,N′-dichloro-N-phenylurea;
N,N′-dichloro-N,N′-diphenylurea;
N,N′-dichloro-N-(p-tolyl)urea;
N,N′-dichloro-N-(m-chlorophenyl)-N′-methylurea;
N,N′-dichloro-N,N′-dicyclohexylurea;
N,N′-dichloro-N-isopropyl-N′-(p-tolyl)urea;
N,N′-dichloro-N-phenyl-N′-propylurea;
N,N′-dichloro-N-cyclohexyl-N′-(p-nitrophenyl)urea;
N,N,N′-trichloro-N-methylurea;
N,N,N′-trichloro-N-phenylurea; and the like.

The preferred N-chloro amides which can be employed in this invention generally have the formula

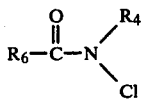

in which R₄ and R₆ are as hereinbefore defined.

Illustrative of these amides are N-chloroacetamide, N-chloropropionamide, N-chloro-N-methylacetamide, N,N-dichloroacetamide, N-chloro-N-cyclohexylacetamide, N-chloro-N-ethylbenzamide, N-chloro-p-chlorobenzamide, N-chloro-p-toluamide, N-chloro-N-phenylpropionamide, N-chloro-N-(m-bromophenyl)-butyramide, N-chlorohexahydrobenzamide, N,2,4-trichloroacetanilide, and the like.

The preferred N-chloro urethans which can be used in preparation of the sulfinyl chlorides in accordance with this invention generally have the formula

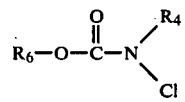

in which R₄ and R₆ are as hereinbefore defined.

Illustrative of these urethans are methyl N,N-dichlorocarbamate ethyl N,N-dichlorocarbamate, phenyl N,N-dichlorocarbamate, cyclohexyl N,N-dichlorocarbamate, methyl N-chlorocarbamate, ethyl N-chlorocarbamate, ethyl N-cyclohexyl-N-chlorocarbamate, phenyl N-chlorocarbamate, phenyl N-phenyl-N-chlorocarbamate, p-tolyl N-chlorocarbamate, m-chlorophenyl N-methyl-N-chlorocarbamate, cyclohexyl N-cyclohexyl-N-chlorocarbamate, isopropyl N-p-tolyl-N-chlorocarbamate, phenyl N-propyl-N-chlorocarbamate, cyclohexyl N-p-nitrophenyl-N-chlorocarbamate, and the like.

The preferred N-chloro sulfonamides which can be used to prepare the sulfinyl chlorides in accordance with this invention have the formula

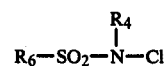

in which R₄ and R₆ are as hereinbefore defined.

Illustrative of the sulfonamides which can be employed as halogenating agents are N,N-dichlorobenzenesulfonamide, N,N-dichloromethanesulfonamide, N,N-dichlorocyclohexanesulfonamide, N,N-dichloro-p-toluenesulfonamide, N-chloromethanesulfonamide, N-cyclohexyl-N-chlorobenzenesulfonamide, N-cyclohexyl-N-chloroethanesulfonamide, N-chlorobenzenesulfonamide, N-phenyl-N-chlorobenzenesulfonamide, N-chloro-p-toluenesulfonamide, N-ethyl-N-chloro-m-nitrobenzenesulfonamide, N-methyl-N-chloro-m-chlorobenzenesulfonamide, N-methyl-N-chloro-p-toluenesulfonamide, N-cyclohexyl-N-chlorocyclohexanesulfonamide, N-p-tolyl-N-chloroisopropanesulfonamide, N-propyl-N-chlorobenzenesulfonamide, N-p-nitrophenyl-N-chlorocyclohexanesulfonamide, and the like.

A further preferred type of N-chloro halogenating agent which can be employed in preparation of the sulfinyl chlorides is a sulfimide of the formula

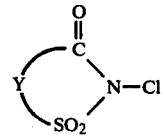

in which Y is o-phenylene, —CH₂—CH₂—, or —CH₂—CH₂—CH₂—. These compounds include o-sulfobenzoic N-chloromide, β-sulfopropionic N-chloroimide, and β-sulfobutyric N-chloroimide.

Also preferred for use as N-chlorohalogenating agents in the preparation of the sulfinyl chlorides in accordance with this invention are N-chloroimides of the formula

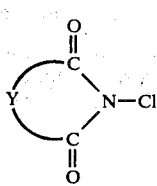

in which Y is o-phenylene, —CH$_2$—CH$_2$—, or —CH$_2$—CH$_2$—CH$_2$—. These compounds include N-chlorophthalimide, N-chlorosuccinimide, and N-chloroglutarimide.

Many of the N-chloro halogenating agents employed in the process of this invention are available commercially, and any of them can be prepared by methods well recognized throughout the chemical arts. Typical of the literature sources which detail preparation of the N-chloro halogenating agents are Bachand et al., *J. Org. Chem.* 39, (1974) pp. 3136–3138; Theilacker et al., *Liebigs Ann. Chem.* 703, (1967) pp. 34–36; and Houben-Weyl, *Methoden der Organischen Chemie*, Volume V/3, pp. 796–810.

N-Chloro halogenating agents which are highly preferred for use i the process of this invention are N-chloro imides, particularly N-chlorosuccinimide or N-chlorophthalimide, and, more particularly, N-chlorophthalimide.

The reaction of the penicillin sulfoxide with the N-chloro halogenating gent is carried out in the presence of an epoxide compound and calcium oxide. Generally, at least 1 mole and up to about 1.5 moles of the halogenating agent are used for each mole of the penicillin sulfoxide ester. An even larger excess of the halogenating agent can be employed; however, non advantage is gained thereby. Preferably, therefore, the ratio of reactants is from about 1.0 to about 1.1 moles of halogenating agent per mole of the penicillin sulfoxide ester. The resulting mixture, preferably dissolved in a suitable inert organic solvent, is heated to a temperature of from about 75° C. to about 135° C. Preferably, the temperature of reaction is from about 100° C. to about 120° C., and, most preferably, is about 102° C. to about 110° C.

By "inert organic solvent" is meant an organic solvent which, under the conditions of sulfinyl chloride formation, does not appreciably react either with the reactants or with the products. Suitable inert organic solvents are those having a boiling point at least as high as the temperature of reaction and include, for example, aromatic hydrocarbons such as benzene, toluenee, ethylbenzene, cumene, and the like; halogenated hydrocarbons such as carbon tetrachloride, chlorobenzene, bromoform, bromobenzene, ethylene dichloride, 1,1,2-trichloroethane, ethylene dibromide, and the like; open chain hydrocarbons, such as heptane, octane, nonane, decane, and the like; and any other appropriate inert solvents. Preferred solvents are those having a boiling point within the range of the temperature at which the reaction is to be carried out, thereby permitting the reaction mixture to be refluxed while retaining temperature control. Particular conditions of reaction include the use of toluene or 1,1,2-trichloroethane as solvent with the temperature of reaction being that developed under reflux conditions.

A requirement of the process of this invention is that the reaction be carried out under anhydrous conditions. It is not intended by the term "anhydrous condition" to mean the total absence of any moisture; instead, this term means the avoidance in the reaction mixture of any substantial amount of moisture. This is accomplished by the exercise of any of the recognized procedures for rendering a reaction system anhydrous. The halogenating agent, since it generally will react with water, normally will not be the source of moisture in the reaction mixture; typically, any excessive quantity of moisture in the reaction system arises from the presence of moisture in the solvent which is employed. Generally, therefore, the solvent is pretreated to remove residual amounts of water. The solvent can be rendered anhydrous to the extent herein contemplated by contacting it prior to use in the reaction with a drying agent which will bind moisture and thereby effectively remove it from the solvent. Typical such drying agents include anhydrous sodium sulfate, magnesium sulfate, sodium carbonate, potassium carbonate, calcium carbide, calcium chloride, calcium hydride, potassium sulfate, calcium oxide, molecular sieeves, particularly types 3A and 4A, and the like.

In the event that the solvent is one with which water will azeotrope, moisture can be removed by subjecting the solvent to conditions of reflux using known types of chemical equipment including the usual Dean-Stark trap or the Barrett types of water traps which collect the moisture as it azeotropes out of the solvent medium.

The penicillin sulfoxide ester starting material itself may contain moisture. This can be removed by subjecting the penicillin sulfoxide to any of the typical drying techniques, including in vacuo drying in an oven at a low temperature up to about 50° C. Additionally, the penicillin sulfoxide ester can be added to the solvent and the mixture subjected to azeotropic water removal.

The mixture containing the penicillin sulfoxide ester, the N-chloro halogenating agent, the epoxide compound, and calcium oxide, generally is heated at a temperature in the defined range for a period of from about 0.5 to about 4 hours, and preferably from about 1 to about 2 hours, after which time the sulfinyl chloride can be isolated from the reaction mixture. Although the sulfinyl chloride can be isolated from the reaction mixture, it is not essential that it be isolated from the reaction mixture prior to being subjected to further reaction. As indicated hereinabove, the sulfinyl chloride can be employed as an intermediate in the preparation of a 3-exomethylenecepham sulfoxide. When this is intended, although the sulfinyl chloride need not itself be isolated, the sulfinyl chloride reaction mixture must first be treated in a manner to be further described hereinafter before it can be used in preparation of the 3-exomethyleneceham sulfoxide.

As a portion of the disclosure provided in copending Application Ser. No. U.S. Pat. No. 673,017 U.S. Pat. 4,081,440 filed Apr. 2, 1976, it was indicated that in many instances it is desirable to include a non-alkaline acid scavenger in the reaction mixture. This is recommended on the basis that, for some reason, not yet understood, small amounts of hydrogen chloride, detrimental to the reaction, can be liberated to the reaction system. A non-alkaline acid scavenger will remain entirely inert in the normal, hydrogen chloride-free reaction medium in which the sulfinyl chloride is generated; however, it will become activated to the extent necessary to react with any hydrogen chloride which may be formed and thereby to remove it from the reaction medium.

Typical disclosed non-alkaline acid scavengers include epoxide compounds such as ethylene oxide, propylene oxide, 1,2-epoxybutane, epichlorohydrin, 1,2-epoxy-3-phenoxy-propane, and the like. These substances exhibit non-alkaline properties but, nevertheless, will react with a remove acidic substances from a reaction system.

It now has been discovered that, when the sulfinyl chloride preparation is carried out in the presence of a non-alkaline acid scavenger epoxide compound, and particularly one selected from the group consisting of propylene oxide and 1,2-epoxybutane, the addition to the reaction mixture of calcium oxide is highly advantageous in promoting conversion of the penicillin sulfoxide to the desired sulfinyl chloride. This is especially evident in those instances in which the scale of the reaction contemplates about 50 g. or more of the penicillin sulfoxide starting material. It has been discovered that the extent of conversion of the penicillin sulfoxide to the sulfinyl chloride when carried out in accordance with the process described in co-pending Application Ser. No. 673,017 U.S. Pat. No. 4,081,440 filed Apr. 2, 1976, decreases significantly with increasing scale of reaction. The advantage of this invention therefore is directed in particular to those preparation of sulfinyl chloride in which at least about 50 g. of penicillin sulfoxide starting material are employed.

The amount of epoxide compound which is employed in the sulfinyl chloride preparation need be an amount sufficient at least to account for any hydrogen chloride which may be formed. Although an excess of the epoxide compound therefore is not essential, an amount of about 2 to about 10 moles, and particularly about 5 moles, of the epoxide compound per mole of the penicillin sulfoxide customarily is employed. Such an excess can be employed without adverse consequence in the preparation of the sulfinyl chloride. However, the presence of the excess epoxide compound will become significant in those instances in which the reaction mixture containing the sulfinyl chloride product is itself used in conversion to the corresponding 3-exomethylenecepham sulfoxide. Therefore, it is highly preferred that, prior to ring-closure using a Friedel-Crafts catalyst, any excess epoxide compound as well as any product formed by reaction of the epoxide compound with hydrogen chloride be separated from the sulfinyl chloride reaction mixture. This generally can be accomplished by distillation of the reaction mixture under conditions and for a period sufficient to ensure removal of the excess epoxide.

As noted, this invention contemplates the presence of a combination of calcium oxide and the epoxide compound during reaction of the penicillin sulfoxide with the N-chloro halogenating agent to form the sulfinyl chloride. The amount of calcium oxide generally will range from about 100 g. to about 500 g; and preferably from about 200 g. to about 250 g., per mole of the penicillin sulfoxide starting material. The calcium oxide is present throughout the time of the sulfinyl chloride preparation and during removal of excess epoxide compound. It is then readily removed by filtration from the residual reaction mixture.

A typical preparation of a sulfinyl chloride in accordance with the process of this invention is accomplished by mixing calcium oxide and molar equivalents of the penicillin sulfoxide and the N-chloro halogenating agent in a suitable pre-dried solvent. Propylene oxide or 1,2-epoxybutane then is added, and the resulting mixture is heated to the desired temperature of reaction for the intended period of reaction. Preferably, the solvent which is employed is one which, in conjunction with the amount of proylene oxide or 1,2-epoxybutane which is present, permits the temperature of reaction to be achieved and maintained by reflux of the reaction mixture. Toluene is a suitable such solvent. Upon completion of the reaction time, the reaction mixture is rapidly distilled to remove excess epoxide. The remaining mixture is cooled and filtered. Upon evaporation of the solvent, the sulfinyl chloride product is recovered.

Examples of sulfinyl chlorides prepared by the process of this invention includes:

t-butyl 3-methyl-2-(2-chlorosulfinyl-4-oxo-3-phenylacetamido-1-azetidinyl)-3-butenoate;

t-butyl 3-methyl-2-(2-chlorosulfinyl-4-oxo-phenoxyacetamido-1-azetidinyl)-3-butenoate;

benzyl 3-methyl-2-(2-chlorosulfinyl-4-oxo-3-formamido-1-azetidinyl)-3-butenoate;

2,2,2-trichloroethyl 3-methyl-2-(2-(2-chlorosulfinyl-4-oxo-3-acetamido-1-azetidinyl)-3-butenoate;

p-nitrobenzyl 3-methyl-2-(2-chlorosulfinyl-4-oxo-3-butyramido-1-azetidinyl)-3-butenoate;

p-methoxybenzyl 3-methyl-2-(2-chlorosulfinyl-4-oxo-3-chloroacetamido-1-azetidinyl)-3-butenoate;

benzhydryl 3-methyl-2-[2-chlorosulfinyl-4-oxo-3-cyanoacetamido-1-azetidinyl]-3-butenoate;

p-nitrobenzyl 3-methyl-2-[2-chlorosulfinyl-4-oxo-3-(4-nitrobenzyloxycarbamido)-1-azetidinyl]-3-butenoate;

t-amyl 3-methyl-2-(2-chlorosulfinyl-4-oxo-3-benzyloxycarbamido-1-azetidinyl)-3-butenoate;

t-hexyl 3-methyl-2-[2-chlorosulfinyl-4-oxo-3-(t-butyloxycarbamido)-1-azetidinyl]-3-butenoate;

2-iodoethyl 3-methyl-2-[2-chlorosulfinyl-4-oxo-3-(2',2',2'-trichloroethoxycarbamido)-1-azetidinyl]-3-butenoate;

acetoxymethyl 3-methyl-2-[2-chlorosulfinyl-4-oxo-3-(4'-methoxybenzyloxycarbamido)-1-azetidinyl]-3-butenoate;

benzyl 3-methyl-2-[2-chlorosulfinyl-4-oxo-3-(2'-thienylacetamido)-1-azetidinyl]-3-butenoate;

t-amyl 3-methyl-2-(2-chlorosulfinyl-4-oxo-3-benzamido-1-azetidinyl)-3-butenoate;

phenacyl 3-methyl-2-[2-chlorosulfinyl-4-oxo-3-(4'-chlorobenzamido)-1-azetidinyl]-3-butenoate;

p-chlorophenacyl 3-methyl-2-[2-chlorosulfinyl-4-oxo-3-(3'-formyloxybenzamido)-1-azetidinyl]-3-butenoate;

pivaloyloxymethyl 3-methyl-2-[2-chlorosulfinyl-4-oxo-3-(4'-nitrobenzamido)-1-azetidinyl]-3-butenoate;

isopropyl 3-methyl-2-[2-chlorosulfinyl-4-oxo-3-(2'-cyanobenzamido)-1-azetidinyl]-3-butenoate;

succinimidomethyl 3-methyl-2-[2-chlorosulfinyl-4-oxo-3-(4'-trifluoromethylbenzamido)-1-azetidinyl]-3-butenoate;

phthalimidomethyl 3-methyl-2-[2-chlorosulfinyl-4-oxo-3-(3'-methylbenzamido)-1-azetidinyl]-3-butenoate;

t-butyl 3-methyl-2-[2-chlorosulfinyl-4-oxo-3-(2'-methoxybenzamido)-1-azetidinyl]-3-butenoate;

p-nitrobenzyl 3-methyl-2-[2-chlorosulfinyl-4-oxo-3-(1',4'-cyclohexadienylacetamido)-1-azetidinyl]-3-butenoate;

2,2,2-trichloroethyl 3-methyl-2-[2-chlorosulfinyl-4-oxo-3-(2'-thienylacetamido)-1-azetidinyl]-3-butenoate;

p-methoxybenzyl b 3-methyl-2-(2-chlorosulfinyl-4-oxo-3-phenylacetamido-1-azetidinyl)-3-butenoate;

2,2,2-trichloroethyl 3-methyl-2-(2-chlorosulfinyl-4-oxo-3-phenoxyacetamido-1-azetidinyl)-3-butenoate;

p-nitrobenzyl 3-methyl-2-[2-chlorosulfinyl-4-oxo-3-(2',5'-dichlorophenylacetamido)-1-azetidinyl]-3-butenoate;

benzyl 3-methyl-2-[2-chlorosulfinyl-4-oxo-3-(3'-bromophenoxyacetamido)-1-azetidinyl]-3-butenoate;

t-butyl 3-methyl-2-[2-chlorosulfinyl-4-oxo-3-(4'-chloroacetoxyphenylacetamido)-1-azetidinyl]-3-butenoate;

isobutyl 3-methyl-2-[2-chlorosulfinyl-4-oxo-3-(3'-formyloxyphenoxyacetamido)-1-azetidinyl]-3-butenoate;

p-nitrobenzyl 3-methyl-2-[2-chlorosulfinyl-4-oxo-3-(2'-nitrophenylacetamido)-1-azetidinyl]-3-butenoate;

p-methoxybenzyl 3-methyl-2-[2-chlorosulfinyl-4-oxo-3-(4'-nitrophenoxyacetamido)-1-azetidinyl]-3-butenoate;

benzhydryl 3-methyl-2-[2-chlorosulfinyl-4-oxo-3-(3'-cyanophenylacetamido)-1-azetidinyl]-3-butenoate;

p-bromophenacyl 3-methyl-2-[2-chlorosulfinyl-4-oxo-3-(2'-cyanophenoxyacetamido)-1-azetidinyl]-3-butenoate;

propionoxymethyl 3-methyl-2-[2-chlorodulfinyl-4-oxo-3-(4'-trifluoromethylphenylacetamido)-1-acetidinyl]-3-butenoate;

2,2,2-tribromoethyl 3-methyl-2-[2-chlorosulfinyl-4-oxo-3-(3'-trifluoromethylphenoxyacetamido)-1-azetidinyl]-3-butenoate;

2-iodoethyl 3-methyl-2-[2-chlorosulfinyl-4-oxo-3-(2'-ethylphenylacetamido)-1-azetidinyl]-3-butenoate;

acetoxymethyl 3-methyl-2-[2-chlorosulfinyl-4-oxo-3-(4'-isopropylphenoxyacetamido)-1-azetidinyl]-3-butenoate;

t-butyl 3-methyl-2-[2-chlorosulfinyl-4-oxo-3-(3'-ethoxyphenylacetamido)-1-azetidinyl]-3-butenoate;

p-nitrobenzyl 3-methyl-2-[2-chlorosulfinyl-4-oxo -3-(4'-isopropoxyphenoxyacetamido)-1-aze tidinyl]-3-butenoate;

p-nitrobenzyl 3-methyl-2-[2-chlorosulfinyl-4-oxo-3-(α-formyloxyphenylacetamido)-1-azetidinyl]-3-butenoate;

p-methoxybenzyl 3-methyl-2-[2-chlorosulfinyl-4-oxo-3-(α-benzhydryloxyphenylacetamido)-1-azetidinyl]-3-butenoate;

benzyl 3-methyl-2-[2-chlorosufinyl-4-oxo-3-(2-thienyl-α-benzyloxyacetamido)-1-azetidinyl]-3-butenaote;

benzhydryl 3-methyl-2-[2-chlorosulfinyl-4-oxo-3-(α-benzhydryloxyphenylacetamido)-1-azetidinyl]-3-butenoate;

p-nitrobenzyl 3-methyl-2-[2-chlorosulfinyl-4-oxo-3-(α-benzyloxycarbonylaminophenylacetamido)-1-azetidinyl]-3-butenoate;

t-butyl 3-methyl-2-[2-chlorosulfinyl-4-oxo-3-(α-t-butyloxycarbonylaminophenylacetamido)-1-azetidinyl]-3-butenoate;

p-nitrobenzyl 3-methyl -2-[2-chlorosulfinyl-4-oxo-3-(2-thienyl-α-p-nitrobenzyloxycarbonylaminoacetamido)-1-azetidinyl]-3-butenoate;

p-nitrobenzyl 3-methyl-2-[2-chlorosulfinyl-4-oxo-3-(2'-thienylacetamido)-1-azetidinyl]-3-butenoate;

benzyl 3-methyl-2-[2-chlorosulfinyl-4-oxo-3-(3'-thienylacetamido)-1-azetidinyl]-3-butenoate;

p-methoxybenzyl 3-methyl-2-[2-chlorosulfinyl-4-oxo-3-phenylthioacetamido-1-azetidinyl]-3-butenoate;

benzhydryl 3-methyl-2-[2-chlorosulfinyl-4-oxo-3-(2',5'-dichlorophenylthioacetamido)-1-azetidinyl]-3-butenoate;

t-butyl 3-methyl-2-[2-chlorosulfinyl-4-oxo-3-(4'-chloroacetoxyphenylthioacetamido)-1-azetidinyl]-3-butenoate;

p-nitrobenzyl 3-methyl-2-[2-chlorosulfinyl-4-oxo-3-(3'-nitrophenylthioacetamido)-1-azetidinyl]-3-butenoate;

p-nitrobenzyl 3-methyl-2-[2-chlorosulfinyl-4-oxo-3-(2'-cyanophenylthioacetamido)-1-azetidinyl]-3-butenoate;

p-methoxybenzyl 3-methyl-2-[2-chlorosulfinyl-4-oxo-3-(4'-trifluoromethylphenylthioacetamido)-1-azetidinyl]-3-butenoate;

benzyl 3-methyl-2-[[3-chlorosulfinyl-4-oxo-3-[3'-(2''-chlorophenyl)-5'-methyl isoxazol-4'-ylcarbamido]-1-azetidinyl]]-3-butenoate;

acetoxymethyl 3-methyl-2-[2-chlorosulfinyl-4-oxo-3-(3'-methylphenylthioacetamido)-1-azetidinyl]-3-butenoate;

2.2.2-trichloroethyl 3-methyl-2-[2-chlorosulfinyl-4-oxo-3-(4'-methoxyphenylthioacetamido)-1-azetidinyl]-3-butenoate; and the like.

As hereinbefore noted, the sulfinyl chlorides produced by the process of this invention are useful as intermediates and can be ring-closed to the corresponding 3-exomethylenecepham sulfoxides by subjection of the sulfinyl chloride to a Friedel-Crafts catalyst, such as, for example, stannic chloride.

The cyclization generally is carried out in the presence of a dry inert organic solvent. Any of a wide variety of dry inert organic solvents may be employed as the medium for the cyclization reaction. By "inert organic solvent" is meant an organic solvent which, under the conditions of cyclization, does not appreciably react either with the reactants or the products. Since the sulfinyl chloride starting material, like other acid chloride reagents, is susceptible to hydrolysis and to attack by other protic compounds, e.g. alcohols and amines, moisture and other such protic compounds should be excluded from the reaction medium. A dry aprotic organic solvent thus is preferred. Trace amounts of water, such as may be present in commercially dried solvents, can be tolerated; however, it is preferred that cyclization be carried out under anhydrous conditions. Suitable solvents include, for example, aromatic compounds including aromatic hydrocarbons, such as, benzene, toluene, xylene, and the like, as well as chlorobenzene, nitrobenzene, nitromesitylene, and the like; halogenated aliphatic hydrocarbons, such as chloroform, methylene chloride, carbon tetrachloride, 1,2-dichloroethane (ethylene chloride), 1,1,2-trichloroethane, 1,1-dibromo-2-chloroethane; and other solvents recognized by those skilled in the art as suitable for Friedel-Crafts type reactions, including, among others, carbon disulfide and nitromethane. Preferred solvents are aromatic hydrocarbons, particularly benzene, toluene, and xylene, and, most particularly, toluene, and halogenated aliphatic hydrocarbons, particularly methylene chloride and ethylene chloride.

Any of the solvents which are employed in the preparation of the sulfinyl chloride can also be used in carrying out the cyclization of the azetidinone sulfinyl chloride. Thus, the sulfinyl chloride need not be isolated from the reaction mixture in which it was generated before cyclization can be carried out. However, when this method of cyclization is employed, it is essential that the reaction mixture containing the sulfinyl chloride starting material be treated prior to use to remove first, the epoxide compound and then the calcium oxide, and any reaction products thereof. This can conveniently be achieved by first distilling the reaction mixture to remove the low-boiling epoxide, and then filtering the mixture to remove the calcium oxide as well as all other insolubles. The resulting filtrate then is ready for use in the Friedel-Crafts catalyzed cyclization.

Cyclization of the azetidinone sulfinyl chloride is carried out at a temperature ranging from about −20° C. to about +100° C., and preferably, between about 10° C. and 60° C. The optimum temperature of cyclization is determined by the particular Friedel-Crafts catalyst which is employed. For example, when stannic chloride is employed, cyclization proceeds at room temperature, whereas, when other Friedel-Crafts catalysts are employed, higher temperatures may be required.

In order to ensure completion of the cyclization reaction, at least one equivalent of the Friedel-Crafts catalyst is employed for each mole of the sulfinyl chloride starting material. Using less than one equivalent of the Friedel-Crafts catalyst reagent may result in a lower conversion of product and thus may leave a portion of the sulfinyl chloride unreacted. Typically, the amount of Friedel-Crafts catalyst reagent which is employed will range from slightly over one equivalent to about two equivalents per mole of the sulfinyl chloride. Preferably about 1.1 equivalents of the catalyst reagent is employed per mole of the sulfinyl chloride.

The time of the reaction generally will range from about 15 minutes to about 2 hours, the reaction time being dependent to some extent upon the particular reactants, the solvents employed, and the temperature at which the reaction is carried out. Usually, the reaction will be completed after the reactants have been maintained in contact at the preferred temperature for about one hour to about 16 hours. The reaction mixture can easily be monitored, for example, by comparative thin-layer chromatography, to determine when the cyclization reaction has reached completion.

Th 3-exomethylenecepham sulfoxides produced by cyclization of the sulfinyl chlorides of this invention can be isolated and purified by employing conventional experimental techniques. These include chromatographic separation, filtration, crystallization, recrystallization and like methods.

The 3-exomethylenecepham sulfoxide cyclization products are useful as intermediates in the preparation of antibiotic compounds. The sulfoxides can be reduced by known procedures, typically with phosphorous trichloride or phosphorous tribromide in dimethylformamide, to provide the corresponding -exomethylenecephams -exomthylenecephams.

The exomethylenecephams can be employed in the preparation of novel cephem antibiotics of the formula

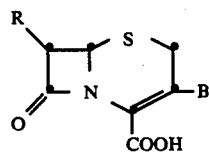

in which B is, for example, chloro, bromo or methoxy. Such chemical conversions of 3-exomethylenecepham compounds have been disclosed in the chemical literature [Robert R. Chauvette and Pamela A. Pennington, *Journal of the American Chemical Society*, 96, 4986 (1974)].

In general, the 3-exomethylenecepham compounds are converted by low temperature ozonolysis to 3-hydroxycephems which, in turn, can be treated with diazomethane at room temperature in tetrahydrofuran containing 1 equivalent of triethylamine to afford the 3-methoxycephem derivatives. The 3-halocephems are derived from the 3-hydroxycephem esters by treatment with a halogenating reagent such as phosphorous trichloride or phosphorous tribromide in N,N-dimethylformamide.

The corresponding cephem acids exhibit potent antibacterial activity. These are available by cleavage of the ester function. Deesterification can be achieved, depending on the nature of the protecting group, by any of several recognized procedures, including (1) treatment with an acid such as trifluoroacetic acid formic acid, hydrochloric acid or the like; (2) treatment with zinc and an acid such as formic acid, acetic acid or hydrochloric acid; or (3) hydrogenation in the presence of palladium, platinum, rhodium or a compound thereof, in suspension, or on a carrier such as barium sulfate, carbon, alumina or the like.

This invention is further illustrated by reference to the comparative examples which follow. It is not intended that ths invention be limited in scope by reason of any of the examples provided herein.

EXAMPLE 1

Preparation of p-Nitrobenzyl 7-Phenoxyacetamido-3-exomethylenecepham-4-carboxylate-1-oxide A. Reaction in the Absence of Calcium Oxide Toluene (1.5 liters) was dried azeotropically with removal of 150 ml. of material. An additional 50 ml. was removed for use in the transfer of reactants to the reaction system. Heatig was discontinued, and 50 grams of p-nitrobenzyl 6-phenoxyacetamido-2,2-dimethylpenam-3-carboxylate-1-oxide and 23 grams of N-chlorophthalimide were added. A Dean-Stark water trap was added to the system, and an approximately 1:1 mixture of calcium chloride and magnesium oxide having a total weight of 14.3 grams was added to the water trap. Heat was reapplied, and 45 ml. of propylene oxide were added, the mixture refluxing at 102° C. The mixture became clear after about 70 minutes. After 75 minutes an nmr was run on a sample of the reaction mixture, and the presence of the sulfinyl chloride intermediate was indicated. After 100 minutes, the water trap containing the calcium chloride and magnesium oxide mixture was replaced by a fresh water trap, and the mixture was allowed to distill. Over the next 35 minutes, 315 ml. of material were removed, the temperature of the reaction mixture rising to 110.5° C. The mixture was then cooled to 10° C. over a 20 minute period. The reaction mixture was filtered, and the filtrate was added to a precooled mixture of 25 ml. of stannic chloride in toluene. The resulting mixture was allowed to stir overnight during which time a red cake formed. The cake was filtered and then was extracted with 250 ml. of acetone and 500 ml. of ethyl acetate. The resulting extract was washed with 1 liter of water and then with 500 ml. of brine. The organic mixture was evaporated to about one-half volume and was allowed to crystallize with cooling. The resulting mixture was filtered, and the solid was dried in vacuo at room temperature to obtain 22.7 grams (45.4%) of the title compound.

B. Reaction in the Presence of Calcium Oxide

Toluene (2.0 liters) was dried azeotropically with removal of 200 ml. of material. An additional 100 ml of toluene was removed for use in transferring reactants to the reaction system. Heating was discontinued, and 50 grams of p-nitro-benzyl 6-phenoxyacetamido-2,2-dimethylpenam-3-carboxylate-1-oxide, 22 grams of N-chlorohthalimide, and 22 grams of calcium oxide were added. Heat was applied, and 35 ml. of propylene oxide were added, providing a reflux temperature of 103°–104° C. The mixture was heated for 75 minutes at 104° C. and then was distilled for 30 minutes with removal of 545 m. of material, the temperature of the reaction mixtue rising to 110° C. The resulting mixture then was cooled to 10° C. and filtered. The filtrate was added to a mixture of 50 ml. toluene and 25 ml. of stannic chloride precooled to 0° C. The resulting mixture then was stirred for 10 hours with formation of a solid. The solid was collected by filtration and then was extracted with a mixture of 500 ml. of ethyl acetate and 250 ml. of acetone. The extract was washed with 500 ml. of water, evaporated to one-half volume, and cooled overnight. The title compound (28.55 g.; 57.1%) was obtained.

EXAMPLE 2

Preparation of p-Nitrobenzyl 7-Phenylacetamido-3-exomethylenecepham-4-carboxylate-1-oxide A. Reaction in the Absence of Calcium Oxide Toluene (2.1 liters) was dried by distillative removal of about 160 ml. of the solvent. An additional 50 ml. of toluene were removed for use in transferring the reactants to the reaction medium. Heating was discontinued, and 17.1 grams (34 mmoles) of p-nitrobenzyl 6-phenylacetamido-2,2-dimethylpeham-3-carboxylate-1-oxide, 7.8 grams (37.4 mmoles) of N-chlorophthalimide, and 12 ml. of propylene oxide were added. The mixture was refluxed at 103° C. for 100 minutes after which distillative removal was begun. A total of 170 ml. of material was removed over about 30 minutes. The resulting mixture was cooled to 0°–5° C. The resulting crystalline phthalimide by-product then was removed by filtration. The filtrate was added to a precooled mixture of 8.5 ml. of stannic chloride in toluene. The mixture was stirred overnight during which time it was permitted to warm to room temperature. The resulting solid was collected by filtration and washed thoroughly with toluene. The solid then was dissolved in a mixture of 85 ml. of acetone and 170 ml. of ethyl acetate. The solution then was extracted twice with 170 ml. of water. The organic layer was separated, evaporated to about one-half volume, cooled to room temperature during which time crystallization occurred. The title compound (4.0 grams; 25%) was recovered by filtration.

B. Reaction in the Presence of Calcium Oxide

The reaction of Part A was repeated with the exception that calcium oxide was included in the reaction mixture. The following amounts of materials were employed: 48.5 grams (100 mmoles) of p-nitrobenzyl 6-phenylaetamido-2,2-dimethylpenam-3-carboxylate-1-oxide; 48 grams of calcium oxide; 22 grams of N-chlorophthalimide; and 35 ml. of propylene oxide. The title compound (14.9 grams; 32.6%) was obtained.

EXAMPLE 3

Preparation of 2,2,2-Trichloroethyl 7-Phenoxyacetamido-3-exomethylenecepham-4-carboxylate-1-oxide A. Reaction in the Absence of Calcium Oxide Two liters of toluene were dried by distillative removal of 200 ml. of the material. Heating was discontinued, and 49.8 grams (100 mmoles) of 2,2,2-trichoroethyl 6-phenoxyacetamido-2,2-dimethylpenam-3-carboxylate-1-oxide and 20.4 grams of N-chlorophthalimide were added. The mixture was heated, and 35 ml. of propyleneoxide were added. The total mixture was refluxed to about 103° C. for about 100 minutes after which 705 ml. of the mixture were removed by distillation over a 35 minute period, the temperature of the mixture rising from 103° C. to 110° C. The mixture was cooled to 5°–10° C. and then was filtered. The filtrate was added to a pre-cooled mixture of 50 ml. of toluene and 25 ml. of stannic chloride. The resulting mixture, blood red in color and devoid of any solid, was stirred for 15 minutes during which time the color changed to a mud brown and a small amount of solid appeared. The mixture was stirred overnight and then was filtered to obtain a light brown granular cake. The cake was dissolved in ethyl acetate. The ethyl acetate solution was washed twice with water. The organic layer then was evaporated to a thick gum. The gum was allowed to stand overnight at room temperature after which methanol was added to the gum. Crystallizaton occurred. The mixture was filtered and washed with methanol to obtain 14.4 grams (28.9%) of the title compound.

B. Reaction in the Presence of Calcium Oxide

The reaction of Part A was repeated with the exception that 25 grams of calcium oxide were included in the reaction mixture. The title compound (18.6 grams; 37.3%) was recovered.

EXAMPLE 4

Preparation of p-Nitrobenzyl 7-Phenoxyacetamido-3-methylenecepham-4-carboxylate-1-oxide (pilot plant scale in stainless steel)

A. Reaction in Absence of Calcium Oxide

To a thirty gallon stainless steel still were added 76 liters of toluene. The toluene was dried by distillative removal of about 19 liters of material. An additional 14 liters of toleune were removed leaving about 43 liters the still. The toleune, under nitrogen, then was cooled to about 70° C., and 1.75 kg. of p-nitrobenzyl 6-phenoxyacetamido-2,2-dimethylpenam-3-carboxylate-1-oxide were added. Heat was added, and, when the temperature of the mixture reached about 85° C., 1,400 ml. of propylene oxide were added. Heating was continued, the mixture reaching 102° C. at reflux. A total of 700 grams of N-chlorophthalimide then was added in 87.5 gram portions at approximately 7 minute intervals. Prior to completion of the addition of the N-chlorophthalimide, 350 ml. of propylene oxide were added. Another 175 ml. of propylene oxide were added approximately 1 hour after completion of N-chlorophthalimide addition. The mixture was refluxed at 100°–102° C. for 2.5 hours following the first addition of N-chlorophthalimide. The mixture, having a volume of 52.5 liters, then was cooled to about 61° C., and concentration of the mixture was begun, the volume of the material upon completion being about 38 liters. The mixture then was filtered into a 30 gallon glass-lined still containing a mixture of 875 ml. of stannic chloride and 13 liters of toluene pre-cooled to −2° C. The temperature rose to +14° C. and was cooled to 0°–5° C. The mixture then was stirred overnight. The resulting red precipitate was filtered, and the solid was dissolved in a mixture of 8.75 liters of acetone and 17.5 liters of ethyl acetate. The solution was washed with 17.5 liters of water and then with 17.5 liters of brine. It was separated, concentrated to 15.5 liters, cooled to 0°–5° C., and stirred overnight. The resulting mixture then was filtered, and the collected solid was washed with 1.75 liters of ethyl acetate and dried at 45°–50° C. to obtain 389.6 grams (23.7%) of the title compound.

B. Reaction In The Presence Of Calcium Oxide

This reaction was carried out under substantially the same conditions as those exmployed in Part A with the exception that the N-chlorophthalimide was added in one portion and the reaction was run in a 75 gallon stainless steel still and was scaled up to the following quantities of materials:

144 liters of toluene (dried by binary distillation);
5.25 kg. of calcium oxide;
5.25 kg. of p-nitrobenzyl 6-phenoxyacetamido-2,2-dimethylpenam-3-carboxylate-1-oxide;
2,415 grams of N-chlorophthalimide;
4.2 liters of propylene oxide;
2,625 ml. of stannic chloride in 39 liters of toluene;
23.6 liters of acetone and 52.5 liters of ethyl acetate;
105 liters of water.

Employing the conditions of Part A on the above quantities there were obtained 2.47 kg. (47.7%) of the title compound.

EXAMPLE 5

Preparation of p-Nitrobenzyl 7-Phenoxyacetamido-3-methylenecepham-4-carboxylate-1-oxide (pilot plant scale in glass)

A. Reaction in absence of calcium oxide

To a 30 gallon glass-lined still were added 56 liters of toluene. The toluene was dried by binary distillation with removal of about 9 liters of distillate. The mixture was cooled to room temperature and was purged with nitrogen. Of the remaining toluene, 17.5 liters were removed to serve as solvent for the N-chlorophthalimide reactant, and an additional 4.4 liters were removed to be used as transfer rinses. The remaining toluene was heated, and, upon reaching about 85° C., 1.75 kg. of p-nitrobenzyl 6-phenoxyacetamido-2,2-dimethylpenam-3-carboxylate-1-oxide were added. Upon reaching about 90° C., 1,400 ml. of propylene oxide were added after which 700 grams of N-chlorophthalimide in 17.5 liters of toluene were added over a period of about 70 minutes. During the addition of the N-chlorophthalimide solution, an additional 350 ml. of propylene oxide were added. Upon completion of the N-chlorophthalimide addition, another of 175 ml. of propylene oxide followed by a further 150 ml. of the propylene oxide were added. The resulting mixture, having a reflux temperature of about 102°–103° C., was heated at reflux for a total of 3 hours and 40 minutes after initial addition of the N-chlorophthalimide. The mixture then was permitted to cool. Upon reaching about 43° C., the mixture was concentrated in vacuo until the volume had been reduced to about 42 liters. The mixture then was filtered, and the filtrate was added to a 30 gallon glass-lined still. To the mixture then were added 858 ml. of stannic chloride, the temperature of the mixture rising from 14° C. to 17° C. The mixture was stirred overnight during which time a red precipitate formed. The precipitate was filtered and was washed with about 4 liters of toleune. The red precipitated then was dissolved in 8.75 liters of acetone. Ethyl acetate (17.5 liters) and water (17.5 liters) then were added. The resulting mixture was stirred and then was separated. The organic layer was washed with 1.75 liters of brine and then concentrated to about 16 liters. The concentrate was cooled to 0°–5° C. and was stirred overnight. The resulting mixture was filtered, and the collected solid was washed with 1 liter of ethyl acetate and vacuum dried at 40°–45° C. to obtain 70.16 grams (4.1%) of the title compound.

B. Reaction in the Presence of Calcium Oxide

To a 200 gallon glass-lined still were added 400 liters of binary-dried toluene. To the toluene then were added 14.6 kg. of calcium oxide, 14.6 kg. of p-nitrobenzyl 6-phenoxyacetamido-2,2-dimethylpenam-3-carboxylate-1-oxide, and 6.67 kg. of N-chlorophthalimide. The mixture was heated to 100° C., and 11.68 liters of propylene oxide were added over a 4 minute period. The mixture was refluxed at a temperature of 102°–103° C. for about 90 minutes and then was concentrated over a period of about 45 minutes. About 71 liters of material were removed, and the temperature of the mixture rose from about 103° C. to about 110°–111° C. The mixture then was cooled to about 95° C. and was filtered into a mixture of 7.3 liters of stannic chloride in 108 liters of toluene, the total having been cooled to −6° C. Upon completion of the filtration, an additional 30 liters of toluene were added to facilitate complete transfer of the mixture. The mixture then was allowed to stir overnight at a temperature of from about 17°–20° C. The resulting solid was collected by filtration and was dissolved in 73 liters of acetone. To the acetone solution then were added 146 liters of ethyl acetate followed by 292 liters of water. The mixture was stirred for 5 minutes and then was separated. The organic layer was concentrated in vacuo to about 135 liters, cooled to 0°–5° C., and maintained at that temperature overnight. The resulting mixture was filtered, and the collected solid was washed with 25 liters of ethyl acetate and dried at 50° C. to obtain 6.8 kg. (46.9%) of the title compound.

EXAMPLE 6

Preparation of p-Nitrobenzyl 7-Phenoxyacetamido-3-methylenecepham-4-carboxylate-1-oxide A. Reaction in the Absence of Calcium Oxide Two liters of toluene were dried by distillative removal of 200 ml. of the material. Heating was discontinued, and 50 grams of p-nitrobenzyl 6-phenoxyacetamido-2,2-dimethylpenam-3-carboxylate-1-oxide and 23 grams of N-chlorophthalimide were added. The mixture was heated, and 35 ml. of 1,2-epoxybutane were added. The total mixture was refluxed at about 108° C. for about 78 minutes after which 440 ml. of the mixture were removed by distillation over a 22 minute period. The mixture was cooled to 10° C. and then was filtered.

The filtrate was added to a pre-cooled mixture of about 40 ml. of toluene and 25 ml. of stannic chloride. The resulting mixture was bright red-orange and contained a granular precipitate. The mixture was stirred for about one hour with ice-bath cooling and then was stirred at room temperature overnight. The mixture was filtered, and the filter cake was dissolved in 150 ml. of methanol. The solution was stirred for 3.5 hours and refrigerated overnight to obtain 22.8 grams (45.6%) of the title compound.

B. Reaction in the Presence of Calcium Oxide

The reaction of Part A was repeated with the exception of 25 grams of calcium oxide was included in the reaction mixture. The title compound (29.4grams; 59.15) was recovered.

EXAMPLE 7

Preparation of p-Nitrobenzyl 7-Phenoxyacetamido-3-methylenecepham-4-carboxylate-1-oxide A. Reaction in the absence of calcium oxide Two liters of toluene were dried by distillative removal of 200 ml. of the material. Heating was discontinued, and 50 grams of p-nitrobenzyl 6-phenoxyacetamido-2,2-dimethylpenam-3-carboxylate-1-oxide and 15.2 grams of N-chlorosuccinimide were added. The mixture was heated, and 35 ml. of propylene oxide were added. The total mixture was refluxed at about 104° C. for about 100 minutes after which 725 ml. of the mixture were removed by distillation over a 35 minute period, the temperature of the reaction mixture rising from about 103° C. to 110.5° C. The mixture was cooled to 10° C. and then was filtered. The filtrate was added to a precooled mixture of 50 ml. of toluene and 25 ml. of stannic chloride. The mixture was stirred overnight and then for 10 minutes at 5°–10° C. The mixture then was filtered, and the collected solid was dissolved in a mixture of 250 ml. of acetone and 500 ml. of ethyl acetate. The solution was washed with 500 ml. of water and evaporated to about one-half volume. No crystallization occurred. The mixture was seeded with a sample of the title compound and refrigerated. However, no crystallization was achieved even with seeding and after three days of refrigeration. The product yield was quite low, probably substantially below 20%.

B. Reaction in the Presence of Calcium Oxide

The reaction of Part A was repeated with the exception that 25 grams of calcium oxide were included in the reaction mixture and 16.6 grams of N-chlorosuccinimide were used. The title compound (23.35 grams; 46.7%) was recovered.

I claim:
1. In a process for preparing a cis sulfinyl chloride of the formula

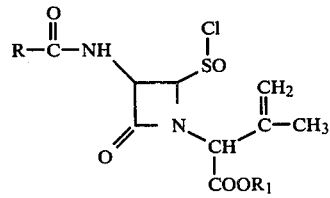

by reacting a penicillin sulfoxide of the formula

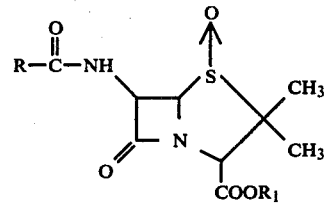

with an N-chloro halogenating agent of the formula

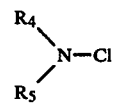

in which $R_4$ is hydrogen, chloro, $C_1$-$C_3$ alkyl, cyclohexyl, phenyl, or phenyl substituted with chloro, bromo, methyl, or nitro, and $R_5$ is $R_6$—X— in which $R_6$ is $C_1$-$C_3$ alkyl, cyclohexyl, phenyl, or phenyl substituted with chloro, bromo, methyl, or nitro, and X is

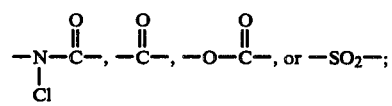

or $R_4$ and $R_5$ taken together with the nitrogen to which they are bonded define a heterocyclic structure of the formula

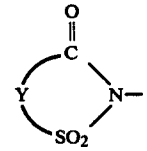

in which Y is o-phenylene or —(CH$_2$)$_n$— in which n is 2 or 3; or a structure of the formula

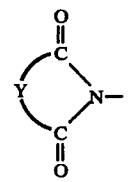

in which Y is as hereinbefore defined; at a temperature of from about 75° C. to about 135° C. in an inert solvent under anhydrous conditions and in the presence of an epoxide compound of the formula

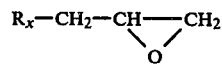

in which $R_x$ is hydrogen or methyl, said epoxide compound being present in an amount at least sufficient to account for any hydrogen chloride which may be formed; in which, in the above formulae, $R_1$ is a carboxylic acid protecting group; and R is
  (a) hydrogen, $C_1$-$C_3$ alkyl, halomethyl, cyanomethyl, benzyloxy, 4-nitrobenzyloxy, t-butyloxy, 2,2,2-trichloroethoxy, 4-methoxybenzyloxy, 3-(2-chlorophenyl)-5-methylisoxazol-4-yl;

(b) the group R' in which R' is phenyl or phenyl substituted with 1 or 2 halogens, protected hydroxy, nitro, cyano, trifluoromethyl, $C_1$-$C_4$ alkyl, (c) a group of the formula R"—(Q)$_m$—CH$_2$— in which R" is R' as defined above, 1,4-cyclohexanidenyl, 2-thienyl, or 3-thienyl; m is 0 or 1; and Q is O or S; subject to the limitation that when m is 1, R" is R'; or (d) a group of the formula

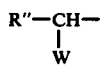

in which R" is as defined above, and W is protected hydroxy or protected amino; the improvement which comprises the step of carrying out the reaction in the presence of from about 100 grams to about 500 grams of calcium oxide per mole of the penicillin sulfoxide.

2. Process of claim 1, in which R is
(a) hydrogen, $C_1$-$C_3$ alkyl, halomethyl, cyanomethyl, benzyloxy, 4-nitrobenzyloxy, t-butyloxy, 2,2,2-trichloroethoxy, 4-methoxybenzyloxy, 3-(2-chlorophenyl)-5-methylisoxazol-4-yl;
(b) the group R' in which R' is phenyl or phenyl substituted with 1 or 2; halogens, protected hydroxy, nitro, cyano, trifloromethyl, $C_1$-$C_4$ alkyl, or $C_1$-$C_4$ alkoxy;
(c) a group of the formula R"—(Q)$_m$—CH$_2$— in which R" is R' as defined above, 1,4-cyclohexadienyl, 2-thienyl, or 3-thienyl; m is 0 or 1; and Q is O or S; subject to the limitation that when m is 1, R" is R'.

3. Process of claim 2, in which R is a group of the formula R"—(Q)$_m$—CH$_2$—.

4. Process of claim 3, in which R" is R'.
5. Process of claim 4, in which R' is phenyl.
6. Process of claim 5, in which m is 0.
7. Process of claim 5, in which m is 1.
8. Process of claim 7, is which Q is oxygen.
9. Process of claim 3, in which R" is 2-thienyl and m is zero.

10. Process of claim 1, in which $R_1$ is $C_4$-$C_6$ tert-alkyl, 2,2,2-trihaloethyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, dimethylallyl, phenacyl, or p-halophenacyl.

11. Process of claim 10, in which $R_1$ is t-butyl, benzyl, p-nitrobenzyl, p-methoxybenzyl, benzhydryl, or 2,2,2-trichloroethyl.

12. Process of claim 1, in which the reaction is carried out in the presence of from about 2 to about 10 moles of the epoxide compound per mole of the penicillin sulfoxide.

13. Process of claim 12, in which the epoxide compound is propylene oxide.

14. Process of claim 12, in which the epoxide compound is 1,2-epoxybutane.

15. Process of claim 1, in which the reaction is carried out in the presence of toluene as solvent.

16. Process of claim 1, in which the N-chloro halogenating agent has the formula

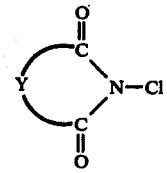

in which Y is o-phenylene or —CH$_2$—CH$_2$—.

17. Process of claim 16, in which the N-chloro halogenating agent is N-chlorosuccinimide.

18. Process of claim 16, in which the N-chloro halogenating agent is N-chlorophthalimide.

* * * * *

UNITED STATES PATENT AND TRADEMARK OFFICE
CERTIFICATE OF CORRECTION

PATENT NO. : 4,165,316
DATED : August 21, 1979
INVENTOR(S) : Ta-Sen Chou

It is certified that error appears in the above—identified patent and that said Letters Patent is hereby corrected as shown below:

Column 1, line 2, "June 12" should read --June 16--.

Column 6, line 68, "of", first occurrence, should read - by -.

Column 10, line 64, "$\beta$" should read --$\gamma$--.

Column 11, line 24, "use i" should read --use in--.

Column 11, line 30, "halogenating gent" should read --halogenating agent--.

Column 11, line 34, "non" should read --no--.

Column 11, line 49, "toluenee," should read --toluene--.

Column 13, line 20, "4081,440" should read --4,081,440--.

Column 14, line 65, "b 3-methyl" should read --3-methyl--.

Column 15, line 23, "chlorodulfinyl" should read --chlorosulfinyl--.

Column 15, line 37, "1-aze tidinyl" should read --1-aze tidinyl]--.

Column 16, line 13, "methyl isoxazol" should read --methylisoxazol--.

UNITED STATES PATENT AND TRADEMARK OFFICE
CERTIFICATE OF CORRECTION

PATENT NO. : 4,165,316
DATED : August 21, 1979
INVENTOR(S) : Ta-Sen Chou

It is certified that error appears in the above—identified patent and that said Letters Patent is hereby corrected as shown below:

Column 17, line 52, "corresponding -exomethylenece-" should read --corresponding 3-exomethylenece--.

Column 17, line 53, "phams exomthylenecephams." should read --phams.--.

Column 18, line 18, "trifluoroacetic acid formic" should read --trifluoroacetic acid, formic--.

Column 18, line 27, "that ths invention" should read --that this invention--.

Column 18, line 39, "Heatig was" should read --Heating was--.

Column 20, line 17, "refluxed to about" should read --refluxed at about--.

Column 20, line 52, "43 liters" should read --43 liters in--.

Column 22, line 45, "for 5minutes" should read --for 5 minutes --.

Column 23, line 16, "59.15)" should read --59.1%)--.

UNITED STATES PATENT AND TRADEMARK OFFICE
CERTIFICATE OF CORRECTION

PATENT NO. : 4,165,316
DATED : August 21, 1979
INVENTOR(S) : Ta-Sen Chou

It is certified that error appears in the above—identified patent and that said Letters Patent is hereby corrected as shown below:

Column 25, line 3, "$C_1$-$C_4$ alkyl," should read --$C_1$-$C_4$ alkyl, or $C_1$-$C_4$ alkoxy;--.

Column 25, line 6, "nidenyl, 2-thienyl," should read --dienyl, 2-thienyl,--.

Column 25, line 27, "1 or 2; halogens," should read --1 or 2 halogens,--.

Column 25, line 28, "trifloromethyl," should read --trifluoromethyl,--.

Column 26, line 8, "$C_2$-$C_6$alkanoyloxymethyl;" should read --$C_2$-$C_6$ alkanoyloxymethyl,--.

Signed and Sealed this

Fourth Day of January 1983

[SEAL]

Attest:

Attesting Officer

GERALD J. MOSSINGHOFF
Commissioner of Patents and Trademarks